United States Patent
Tepper et al.

(10) Patent No.: US 6,261,221 B1
(45) Date of Patent: *Jul. 17, 2001

(54) FLEXIBLE COIL PULSED ELECTROMAGNETIC FIELD (PEMF) STIMULATION THERAPY SYSTEM

(75) Inventors: John C. Tepper, Carrollton; Peter Kuo, Richardson, both of TX (US); William Winstrom, Andover, NJ (US)

(73) Assignee: AMEI Technologies Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 48 days.

(21) Appl. No.: 09/033,045

(22) Filed: Mar. 2, 1998

Related U.S. Application Data (63) Continuation-in-part of application No. 08/742,512, filed on Nov. 1, 1996, now Pat. No. 5,743,844.

(51) Int. Cl.[7] ................ A61N 2/02; A61N 2/04
(52) U.S. Cl. .................. 600/14; 600/13; 607/2
(58) Field of Search .................. 600/9, 13–15; 607/2

(56) References Cited

U.S. PATENT DOCUMENTS

| | | |
|---|---|---|
| 4,266,532 | 5/1981 | Ryaby . |
| 4,456,001 | 6/1984 | Pescatore . |
| 4,501,265 | 2/1985 | Pescatore . |
| 4,548,208 | 10/1985 | Niemi . |
| 4,550,714 | 11/1985 | Talish et al. . |
| 4,561,426 | 12/1985 | Stewart . |
| 4,616,629 | * 10/1986 | Moore . |
| 4,635,643 | 1/1987 | Brown . |
| 4,654,574 | 3/1987 | Thaler . |
| 4,672,951 | 6/1987 | Welch . |
| 4,911,686 | 3/1990 | Thaler . |
| 4,932,951 | 6/1990 | Liboff et al. . |
| 4,974,114 | * 11/1990 | Kammerer ................ 600/9 |
| 5,058,582 | 10/1991 | Thaler . |
| 5,066,272 | 11/1991 | Eaton et al. . |
| 5,088,976 | 2/1992 | Liboff et al. . |
| 5,181,902 | 1/1993 | Erickson et al. . |

(List continued on next page.)

FOREIGN PATENT DOCUMENTS

| | | |
|---|---|---|
| 9300499 | 3/1993 | (DE) . |
| 196 07 704A | 9/1996 | (DE) ................ A61N/2/04 |
| 788813 | 8/1997 | (EP) . |
| 850665 | 7/1998 | (EP) . |
| 2242362 | * 2/1991 | (GB) ................ 600/13 |
| 2 141 030 | 12/1994 | (GB) ................ A61N/1/42 |
| WO8500293 | 1/1985 | (WO) . |
| WO9300131 | 1/1993 | (WO) . |
| WO95/27533 | 10/1995 | (WO) ................ A61N/2/04 |
| 9527533 | * 10/1995 | (WO) ................ A61N/2/04 |

OTHER PUBLICATIONS

PCT International Search Report, Jun. 23, 1999.

Primary Examiner—William E. Kamm
Assistant Examiner—Carl H. Layno
(74) Attorney, Agent, or Firm—Baker Botts L.L.P.

(57) ABSTRACT

A PEMF therapy system uses a single-coil PEMF transducer for generating PEMF stimulation signals. The coil has a "bi-phasic" operation, such that current flows through it in two directions A drive circuit recovers the flyback energy from the transducer coil and dumps voltage to an energy recovery capacitance circuit. The transducer is thereby energized and de-energized to provide the electromagnetic field. The single coil transducer may be fabricated on a flexible substrate and the wiring may be formed with printed circuit techniques. The same concepts may be applied to series-connected coils.

46 Claims, 8 Drawing Sheets

U.S. PATENT DOCUMENTS

| | | |
|---|---|---|
| 5,195,941 | 3/1993 | Erickson et al. . |
| 5,269,747 | 12/1993 | Erickson et al. ......................... 600/14 |
| 5,314,401 | 5/1994 | Tepper ................................... 600/14 |
| 5,318,561 | 6/1994 | McLeod et al. . |
| 5,338,286 | 8/1994 | Abbott . |
| 5,351,389 | 10/1994 | Erickson et al. . |
| 5,401,233 | 3/1995 | Erickson et al. . |
| 5,518,496 | 5/1996 | McLeod et al. . |
| 5,743,844 | 4/1998 | Tepper et al. . |

* cited by examiner

○ PRIMARY
◐ STRUCTURAL WINDING

| PARAMETER | SYMBOL | REQUIREMENT | UNITS |
|---|---|---|---|
| BURST PERIOD | Tbi | 670 ± 3 | ms |
| FIRST PULSE WIDTH (+) | tpwf (+) | 33 ± 3 | μs |
| PULSE WIDTH (+) | tpw (+) | 65 ± 3 | μs |
| PULSE WIDTH (−) | tpw (−) | 195 ± 10 | μs |
| PULSES PER BURST | $N_p$ | 99 | − |

FLEXIBLE COIL PULSED ELECTROMAGNETIC FIELD (PEMF) STIMULATION THERAPY SYSTEM

CROSS-REFERENCE TO RELATED APPLICATION

This application is a continuation-in-part of Ser. No. 08/742,512 filed Nov. 1, 1996, now U.S. Pat. No. 5,743,844, by John C. Tepper, et al., and entitled "High Efficiency Pulsed Electromagnetic Field (PEMF) Stimulation Therapy Method and System"; it is related to co-pending U.S. patent application Ser. No. 09/033,032, entitled "Pulsed Electromagnetic Field (PEMF) Stimulation Therapy System with Bi-Phasic Coil," filed Mar. 2, 1998.

TECHNICAL FIELD OF THE INVENTION

This invention relates generally to pulsed electromagnetic field (PEMF) therapy that promotes healing of skeletal bones and other body tissues, and more particularly to a PEMF system having a high-efficiency single-coil transducer for providing PEMF therapeutic stimulation to a target area of a patient's body.

BACKGROUND OF THE INVENTION

Pulsed electromagnetic fields (PEMF) for treating therapeutically resistant problems of the musculoskeletal system are typically low-energy, time-varying magnetic fields. PEMF therapy has been used to treat non-union bone fractures and delayed union bone fractures. Non-union bone fractures are typically defined as injuries which have not satisfactorily healed within nine months or more after the trauma which caused the injury. Delayed union fractures are typically considered injuries which have not satisfactorily healed within nine months or less after the trauma which caused the associated injury. PEMF therapy has also been used for treatment of corresponding types of body soft tissue injuries.

PEMF therapy has been satisfactorily used in treating spinal fusion, failed arthrodeses, osteonecrosis, and chronic refractory tendinitis, decubitus ulcers and ligament, tendon injuries, osteoporosis, and Charcot foot. During PEMF therapy, an electromagnetic transducer coil is generally placed in the vicinity of the musculoskeletal injury (sometimes referred to as the "target area") such that pulsing the transducer coil will produce an applied or driving field that penetrates to the underlying damaged bone or other body tissue.

Present day PEMF transducers use a substantial amount of energy. In order to account for such energy use, present products may use a rechargeable battery pack, such as either a nickel cadmium or nickel metal hydride battery. Rechargeable battery packs are expensive, heavy, and must be carried by the patient. Many existing PEMF therapy systems must be recharged frequently, which increases the cost and inconvenience of operating such PEMF therapy systems.

The weight of many PEMF bone growth stimulators is generally proportional to the size of the batteries used to power the electrical circuitry as well as by the windings used to generate the output signal. Patient comfort while using such devices is often inversely proportional to the weight. Reducing the battery size and weight will help to reduce the weight and cost of such equipment and improve the patient's comfort.

Recently, ultrasound-based equipment has been used to accelerate healing of body tissue. Ultrasound therapy may also be used for treating non-union and delayed union fractures.

SUMMARY OF THE INVENTION

Various aspects of the invention are directed to a PEMF therapy system having a transducer coil for generating a PEMF signal. The PEMF therapy system includes a drive circuit for recovering flyback energy from the transducer coil and dumping a voltage equal to a predetermined amount, such as four times the battery voltage, for permitting sequencing of the current through the transducer coil in both a first, positive direction and a second, negative direction.

The invention eliminates the need for a secondary coil to recover energy and thereby reduces overall weight and power consumption. The flyback energy of the transducer coil is dumped to an energy recovery capacitance circuit that provides an energy recovery voltage. This voltage is available to supply current during the energize phase of the transducer energize/recover cycle. By having a recovery voltage equal to approximately four times the battery voltage available, current through the transducer coil can be sequenced, in much the same way as is done with a full-bridge or half-bridge circuit, to go in both directions. Therefore, for a given magnetic field strength (PEMF output signal strength), the peak current can be cut in half, resulting in a factor of four reduction in $I^2R$ (energy) loss. The drive circuit, instead of using a separate voltage boost supply circuit, uses its own flyback pulse to provide the recovery voltage. Energy recovery without a secondary coil is also more efficient because there are no coupling losses that arise with a secondary coil (i.e., there is no leakage inductance). In addition, a transducer coil incorporating teachings of the present invention possesses technical advantages of being simpler and less expensive to manufacture.

For example, the transducer coil used to generate the desired PEMF may have fewer windings. Thus, there are fewer electrical connections. This makes the resulting PEMF device more reliable while also being more energy efficient.

Another advantage of the invention is that the use of a single coil sufficiently reduces the size and weight of the device such that it is practical to locate its drive electronics in a small housing proximate to the coil. No interconnecting cables or connectors are required to connect the drive electronics with the primary coil or winding.

Another advantage is that coil heat losses are minimized, and the wire gauge may be smaller. This further helps to make the resulting PEMF transducer lighter and economical to manufacture. The ultimate result is, therefore, a more comfortable, less expensive PEMF therapy system.

Because the PEMF transducer is more energy efficient, it is possible to use a smaller, lighter, non-rechargeable battery. The present invention may use, for example, a commercially-available nine-volt lithium or alkaline non-rechargeable battery.

A particular embodiment of the invention has a flexible transducer coil, and is especially useful for treating soft tissue. The transducer may be placed in or on a cast or bandage covering the location to be treated. It may remain in place until the cast or bandage is removed from the patient.

An advantage of this flexible transducer embodiment is that the PEMF therapy system may be started by the physician and will continue to operate for a predetermined treatment cycle such as four hours per day until the cast has been removed. As a result, patient intervention is not required to ensure that the desired treatment cycle is applied to the target area.

BRIEF DESCRIPTION OF THE DRAWINGS

For a more complete understanding of the present invention and the advantages thereof, reference is now made to the following description which is to be taken in conjunction with the accompanying drawings in which like reference numerals indicate like features and wherein.

DETAILED DESCRIPTION OF ILLUSTRATIVE EMBODIMENTS

Preferred embodiments of the present invention are illustrated in the FIGUREs wherein like numerals refer to like and corresponding parts of the various drawings. This detailed description of illustrative embodiments of the PEMF therapy system is organized as follows:

1. PEMF therapy system and transducer;
2. PEMF transducer design and fabrication;
3. Control and drive electronics;
4. High frequency drive signal operation
5. Soft Tissue Stimulation; and
6. Series-Connected Coils
7. Conclusion.

1. PEMF Therapeutic Stimulation System and Transducer.

The present invention provides a PEMF therapy system having a PEMF transducer that consumes less energy, is lighter, and is easier to use than previous PEMF systems. A PEMF therapy system incorporating teachings of the present invention may be satisfactorily used to treat bone damage, such as non-union fractures, delayed union fractures, and fresh fractures. The PEMF therapy system may also be satisfactorily used to treat damage to other types of body tissues in addition to bone tissue. For purposes of this description, both bone and other body tissue are described generally as "tissue", although use of the invention in U.S. application Ser. No. 08/742,512 (now U.S. Pat. No. 5,743,844) for "bone" and "tissue" are equivalent. U.S. application Ser. No. 08/742,512 (now U.S. Pat. No. 5,743,844) is hereby incorporated herein by reference.

As explained below, all embodiments of the invention use a transducer 20 having a single coil. The coil operates in a "bi-phasic" process in which current passes through it in two directions. Current flows in a first direction to energize the coil. Then, the current flows in a second direction in response to stored energy lost from the first direction current. With the bi-phasic technique, current flows in a positive direction through zero to a negative direction. The result is that the amount of positive voltage, resulting current and, therefore, the energy loss decreases substantially. For the same swing in current, by virtue of going from a negative value to a positive value, approximately a four-fold reduction in energy loss occurs.

Figure 1:
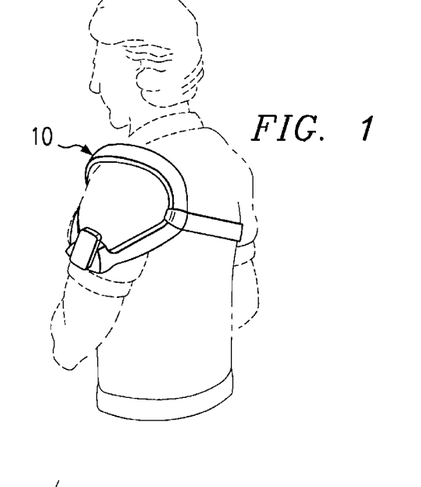
FIGS. 1 through 3 illustrate several different examples of a PEMF therapy system formed according to teachings of the present invention.
Figure 2:
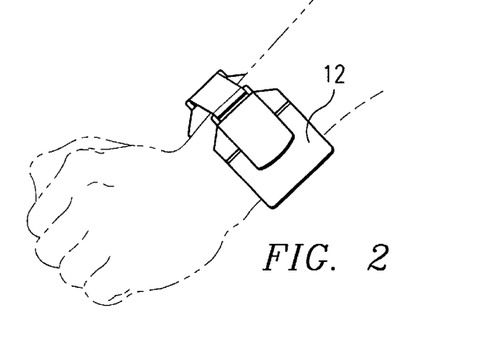
Figure 3:
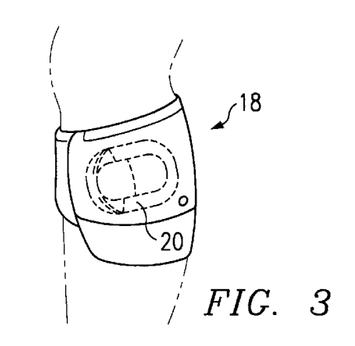

FIGS. 1–3 illustrate exemplary embodiments of the invention, configured to provide PEMF stimulation therapy for the shoulder, the hands, the hip, or essentially any other bone structure of the body to assist in healing objectives such as fusion repair. The PEMF transducer system that the present invention uses may be formed and anatomically contoured for the shoulder, the wrist, the hip or other areas of the skeletal system.

FIG. 1, in particular, shows a contoured triangular PEMF transducer 10 that is anatomically contoured for providing PEMF stimulation therapy to the shoulder area. That is, one side is curved to fit over the top of the shoulder so that corresponding angular areas are positioned in front and in back of the shoulder, with the other sides being curved down along the upper arm. The shoulder transducer is an integral unit including drive electronics and control electronic that may be held in place by a body strap.

FIG. 2 shows placement of a PEMF stimulation therapy device that includes a PEMF stimulation transducer 12 according to the teachings of the present invention, but of a size and shape that best suits the patient's wrist or other limb portion. PEMF transducer drive circuitry and control electronics preferably are made as an integral part of PEMF stimulation transducer 12.

FIG. 3 shows yet another embodiment of the present invention as hip belt PEMF stimulation therapy device 18 that a patient may wear around the waist, the PEMF transducer 20 arranged over the hip area. The drive electronics and control circuitry, again, is an integral part of PEMF stimulation therapy device 18.

Figure 4:
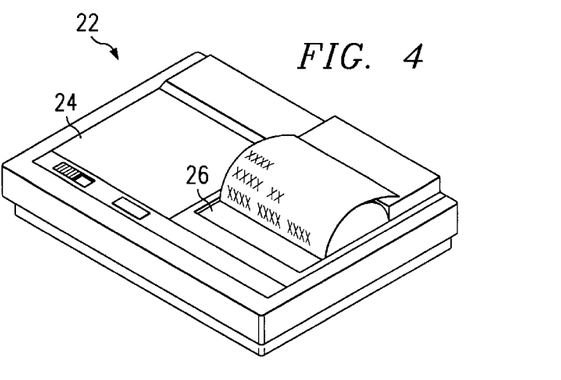
FIG. 4 a read-out unit that may be used for displaying and recording a user's operation of the present invention.

FIG. 4 shows a read-out unit 22 that may be used for displaying and recording a patient's operation of the present invention. The present invention may include, therefore, an extended memory and built-in printer interface 24 for providing the ability to correlate patient usage with desired healing progress and provide results on a paper printout device 26. The system of the present embodiment, for example, may store months of compliance data for developing important correlation data and print out such data using paper printout device 26. Alternatively, data could be uploaded to a computer using appropriate I/O circuitry.

2. PEMF Transducer Design and Fabrication.

Figure 5A:
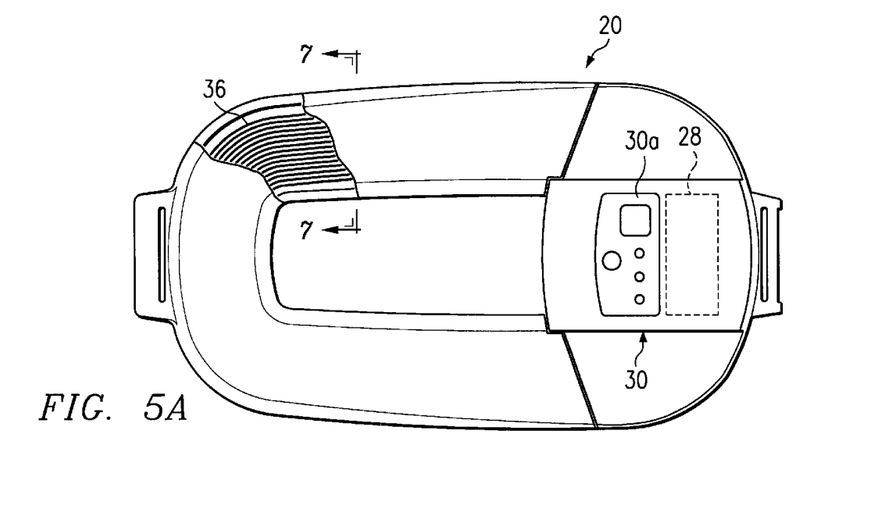
FIGS. 5A, 5B and 6 illustrate an exemplary PEMF stimulation therapy transducer and associated control and drive electronics formed according to the present invention.
Figure 5B:
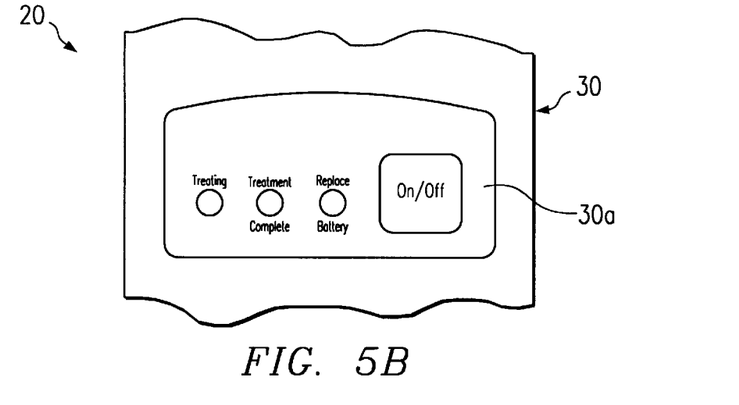
Figure 6:
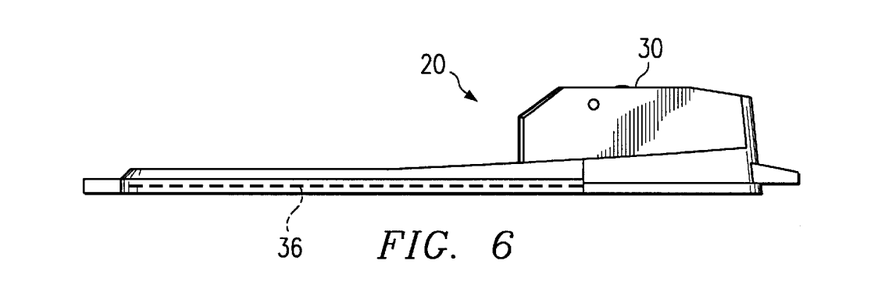

FIGS. 5A, 5B, and 6 illustrate the construction of a PEMF transducer coil and associated electronics that may be, for example, that of PEMF device 18 of FIG. 3. As FIG. 6 shows, PEMF transducer 20 may have a substantially flat cross-sectional profile, which is a result of its flat-wound construction. PEMF transducer 20 is semi-rigid to maintain a desired contour and profile, but is bendable by the patient or health care professional to customize or alter according to the anatomical contour. PEMF transducer 20 has a flat-wound PEMF winding (coil) that may be encapsulated in a shell of a plasticized elastomer material (such as polyurethane) with a selected degree of rigidity.

PEMF transducer 20 includes a PEMF coil that provides the PEMF stimulation signals and drive electronics that assist in tailoring the operation of PEMF transducer 20. Drive electronics 28 is mounted on a circuit board and encased in a plastic shell 30 that covers the end of PEMF coil 36. The circuit board carrying drive electronics 28 is coupled to the PEMF winding of PEMF transducer coil 36, with the winding wires exiting the PEMF transducer coil 36 bundle in the areas 32 and 34.

The control electronics module 28 is integral to PEMF device 18, and includes a PEMF signal processor for providing pulsing current to PEMF transducer 20 at predetermined intervals, thereby activating the PEMF stimulation signal according to a prescribed pre-programmed PEMF regimen.

To implement a PEMF stimulation therapy program, a health care professional determines a regimen of PEMF stimulation of the affected body portion. The prescribed PEMF therapy regimen is translated into a PEMF program, which is programmed into a PEMF memory in control electronics module 28, either during manufacture or subsequently.

For patient use, PEMF transducer 20 may be placed into a Velfoam® pouch or other soft covering preferably using Velcro fasteners of PEMF stimulation therapy device 18, for example. As stated above, the semi-rigid PEMF transducer shell is sufficiently flexible to permit the patient or a health care professional to adjust the anatomical contour. This arrangement relies on a soft but semi-rigid support of the PEMF stimulation therapy device 18, with PEMF transducer 20 being contoured around the affected body part. Once the PEMF stimulation therapy device 18 is in place, the patient starts the PEMF program by turning on control electronics module 28.

In accordance with the stored PEMF therapy program, the PEMF processor correspondingly controls the activation current supplied to PEMF transducer 20, thereby controlling the PEMF stimulation signals in terms of energization time, de-energization time, and duty cycle or repetition rate. In addition to controlling the PEMF therapy, the PEMF processor maintains treatment data that is available on request to the patient (through a small display), and to a health care professional (via an I/O port) for monitoring and analysis.

Figure 7:
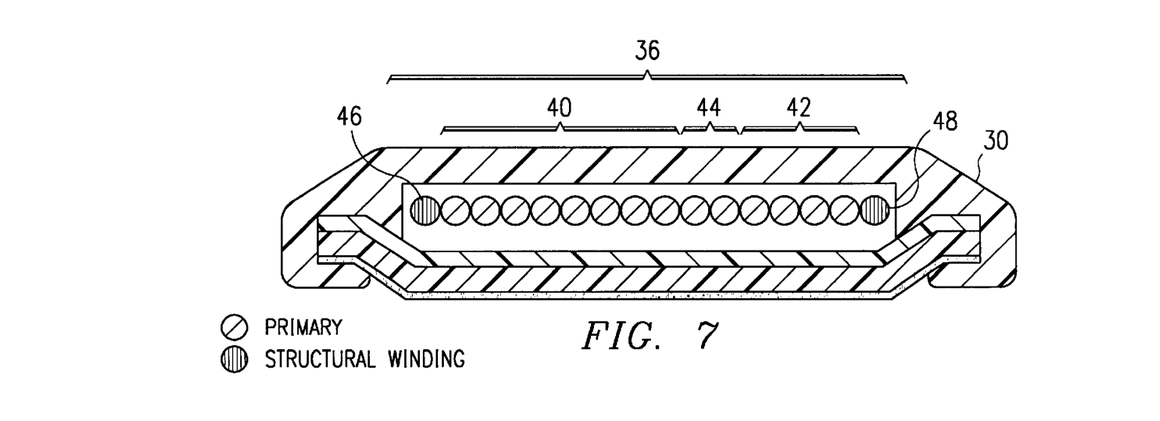
FIG. 7 is an exemplary winding pattern for the PEMF transducer coil circuit of the present invention.

FIG. 7 is a cross-sectional view of PEMF transducer 20 that includes PEMF windings 40 and 42 and 44 surrounded by optional structural windings 46 and 48 and encapsulated in a semi-rigid shell 30.

For an exemplary embodiment, PEMF transducer 20 includes two parallel PEMF windings of about 7 turns each. For the PEMF windings, 18 gauge wire can be used. The approximate dimensions of the winding bundle are 0.75 by 0.12 inches, while the approximate dimensions of the shell are 1.50 by 0.31 inches.

The winding material is a commercially available hookup wire. Shell 30 may be a polyurethane-type elastomer material, also available commercially. Other materials for shell 30 can be used to provide different degrees of transducer-shell rigidity, thereby providing different bracing rigidity characteristics.

The PEMF windings are wound simultaneously in a winding machine around a flat mandrel of the appropriate shape for the transducer. The PEMF windings are maintained in the flat-wound position shown in FIG. 7 by parallel side plates. Once wound, the start and finish wire ends for each winding are cut to provide leads for coupling to the drive electronics, and the winding assembly—winding bundle, mandrel and side plates—is removed from the winding machine. The mandrel includes slots. An adhesive, typically a UV-curable adhesive is placed on the coil through the slots in the mandrel. Then, the entire mandrel assembly is placed within a UV light chamber for curing the unit. The winding bundle is now in a flexible, bonded unit.

Next, the circuit board (not shown) with drive electronics 28 is positioned according to particular desired configuration of the PEMF transducer 20 and may be secured by a variety of mechanisms, such as by adhesive tape, a clamp, or a clam-shell housing made of plastic or another material. The winding leads of the transducer and the wires of a cable are attached to the drive electronics board, such as by soldering.

The winding bundle for PEMF transducer 20 may be placed in a mold. Then, the polyurethane elastomer is molded with the coil in place. This permits separately molding a space in the polyurethane, thermoplastic elastomer, or PVC material so that the mold may be fitted over and encapsulate the winding In one embodiment, a two-component polyurethane elastomer may be separately cast, or made of an injection moldable material such as PVC or Santoprene® (which is a thermoplastic elastomer). Thus, in contrast to molding PEMF transducer 20 in place, the mold is formed separately and PEMF transducer 20 is fit together with the mold.

Finally, after placing PEMF transducer 20 into the molded shell, a backing may be placed on PEMF transducer 20 that is also a flexible plastic, such as Kydex® or some other flexible plastic sheet, and PEMF transducer 20 is then glued or snapped into place. Then PEMF transducer 20 may be introduced into a bending fixture to be bent into the desired anatomical contour. Alternately, PEMF transducer 20 may be covered with a Velfoam® or neoprene sheath for wrapping about a wrist or ankle, such as in the embodiment of FIG. 2.

In still another embodiment, a Metglas® configuration may be used for core coils that form PEMF transducer 20. The Metglas® configuration uses a core holder, which is an essentially flat plastic case that is similar to that in which a videocassette may be packaged, but is somewhat thinner. The material known as Metglas®, which is a flexible ferrite material, which has high permeability, has the ability to store magnetic energy. This allows Metglas® to serve as a core material for the PEMF transducer 20, such as that used for the embodiment of FIG. 2. The Metglas® material may be formed as a core for PEMF transducer 20 in other transducer shapes.

The Metglas® material may be placed in a polyethylene core holder that may then be snapped shut. Then the assembled structure may be placed into a winding machine, which operates as does a lathe with a chuck on each end. This is spun to wind the single winding along the length of the core holder. The core holder is essentially rectangular at this point. The core holder is then removed from the winding machine and bent under heat to form a "U" or horseshoe shape. Then, the core holder is covered with a Velfoam® or other material such as neoprene, to form a sheath over the core holder. Then, a plastic clamp holder may be placed containing the control and drive electronics circuitry on either end. Other embodiments that achieve the purposes of the present invention may also be used.

3. Control and Drive Electronics.

Figure 8:
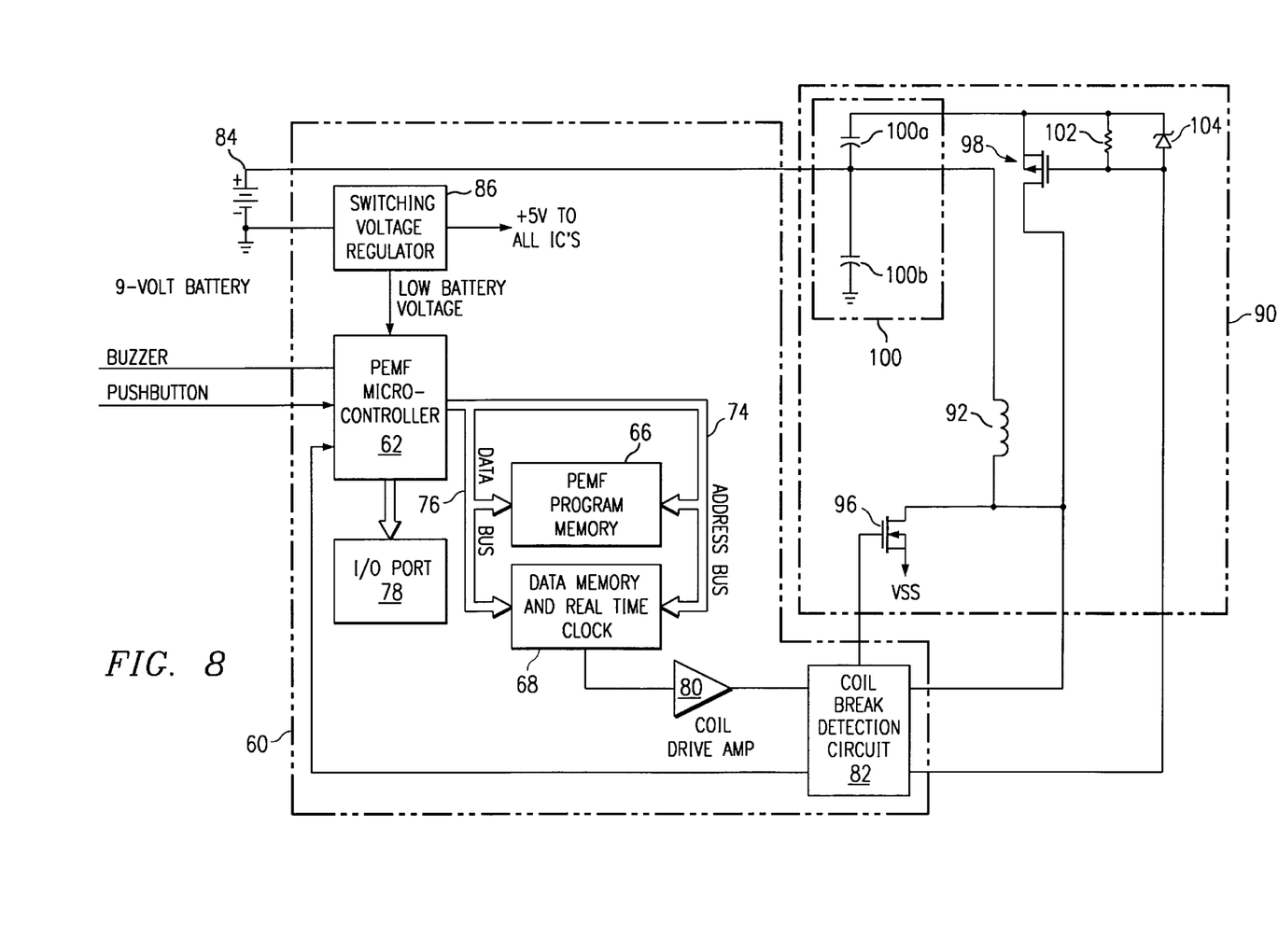
FIG. 8 is a schematic block diagram of the control electronics and the drive electronics for the PEMF transducer system of the present invention.

FIG. 8 is a schematic block diagram of the control electronics and the drive electronics of the present invention, which are physically located respectively in the control electronics module 28 and encapsulated within the shell 30 of the PEMF transducer 20. Control electronics 60 includes a PEMF processor 62, with associated integrated circuit components: a PEMF internal program memory 66, a data memory and real time clock circuit 68. PEMF processor 62 is coupled to these components by address bus 74 and data bus 76. A PEMF program can be loaded into a microcontroller EPROM or other memory and installed as PEMF program memory 66. Alternatively, the PEMF program can be read into the PEMF program memory via an I/O port 78. Data collected during execution of the programmable PEMF program parameters—such as start time, stop time, duration, and daily average—is stored in the data memory 68, and can be read out to a printer (or over a communications link) via the I/O port 78.

The PEMF processor 62 controls transducer drive amplifier 80. The coil drive amplifier controls the energization and de-energization of PEMF transducer 20. Coil break detection circuit 82 senses the resulting electromagnetic fields and provides an appropriate signal to PEMF processor 62. PEMF processor 62 receives power from a power source, such as a nine-volt lithium or alkaline battery 84, for example, through a switching voltage regulator 86 (which also provides +5 volts power to the other integrated circuit components).

PEMF processor 62 and the supporting integrated circuit CMOS logic chips function conventionally and are commercially available. For the exemplary embodiment, PEMF processor 62 may be an Motorola 68HC11 processor. The data memory and real time clock integrated circuit 68 is a Dallas Semiconductor Corporation device, used to store representative data about the patient's use of the PEMF system based on the internally maintained clock and calendar.

As explained further below in connection with FIG. 11, the PEMF program outputs a pair of control signals, each comprising a series of pulse bursts. The two signals have their pulses offset, such that a pulse of one signal is high when a pulse of the other signal is low. These alternating control signals control the drive electronics so that it switches current on and off at the proper times to provide the desired bi-phasic transducer operation.

A feature of the control signals is that at the beginning of one of the pulse bursts, the first pulse is shorter than the other pulses in the same pulse train. Thus, for example, if the first pulse train has pulses with 65 microsecond on and 195 microsecond off times, then the first pulse of the first pulse train is 32.5 microseconds. This first short pulse sets up the magnetic field for the PEMF stimulation therapy signal in the single-winding coil. By turning on the drive circuitry for one-half pulse, energization of the magnetic field takes place to set the PEMF magnetic field away from zero. Then, the next pulse on the other pulse train turns on for 195 seconds. This sets the current so that the drive flyback energy goes in a negative direction. This causes current to flow from an initial negative direction. The current then ramps up through zero and increases from a negative number through zero to a positive number during the pulse. Because the current is changing in the inductor that the PEMF transducer forms, a constant electrical field is induced.

Drive electronics 90 controls activation of PEMF transducer coil 36 and the generation of the PEMF stimulation therapy signals FIG. 8 represents PEMF transducer coil 36 by PEMF winding 92. Drive electronics 90 includes FET switch 96 that connects between coil break detection circuit 82 and PEMF winding 92 and FET switch 98 that connects between capacitor 100 and PEMF winding 92. Capacitor 100, resistor 102 and parallel zener diode 104, control operation of FET switch 98. FET switches 96 and 98 control the PEMF stimulation signal that is output from PEMF winding 92.

In initialization, FET switch 96 is turned on by coil drive amp 80 to present battery voltage across PEMF winding 92 for a period of one-half a normal pulse duration of typically 65 microseconds. Activation current from battery 84, therefore, flows through PEMF winding 92 to generate the PEMF transducer 20 output signals. When FET switch 96 switches off, FET switch 98 switches on to charge capacitor 100 to a voltage equal to four times the battery voltage. This causes the transducer to discharge in the opposite direction during the off period for FET switch 96. Thus, energy recovery occurs without a secondary coil, unlike the case with known systems, and is more efficient. This is because there are no coupling losses that exist with the secondary winding. Since the recovery voltage is four times the available battery voltage, drive circuit 90 permits sequencing of the current through PEMF winding 92 to flow in both directions. Therefore, for a given magnetic field strength, the peak current can be cut in half. This results in a factor of four reduction in $I^2R$ losses, where I is the instantaneous coil current and R is the resistance of the coil winding These are the types of losses that would exist with the use of a secondary winding. With the preferred embodiment of the invention, the voltage $V_{X4}$ may be derived using the flyback pulse from PEMF winding 92, instead of requiring a separate voltage boost circuit. By balancing the capacity of capacitors 100a and 100b, it is possible to eliminate the need for a separate four-times voltage supply circuit.

In the example of FIG. 8, the energy restoring capacitance circuit 100 is comprised of two series connected capacitors 100a and 100b. Their capacitance ratio is at least 1:3, and is the example of this description is 1:10 (in microfarads). Various other capacitor configurations could be used for energy recovery capacitance circuit 100, with the common characteristic that it provide the desired energy restoring voltage, here $V_{X4}$. For example, energy restoring capacitance circuit 100 could be comprised of a capacitor and voltage regulator circuitry.

Coil break detection circuit 82 senses the electromagnetic fields generated during PEMF transducer activation and provides feedback to PEMF microcontroller 62 for monitoring the operation of PEMF stimulation device operation, for example PEMF microcontroller 62 causes appropriate monitoring data to be stored in data memory and real time clock 68, and will initiate an alarm signal in the case of malfunction.

Figure 9:
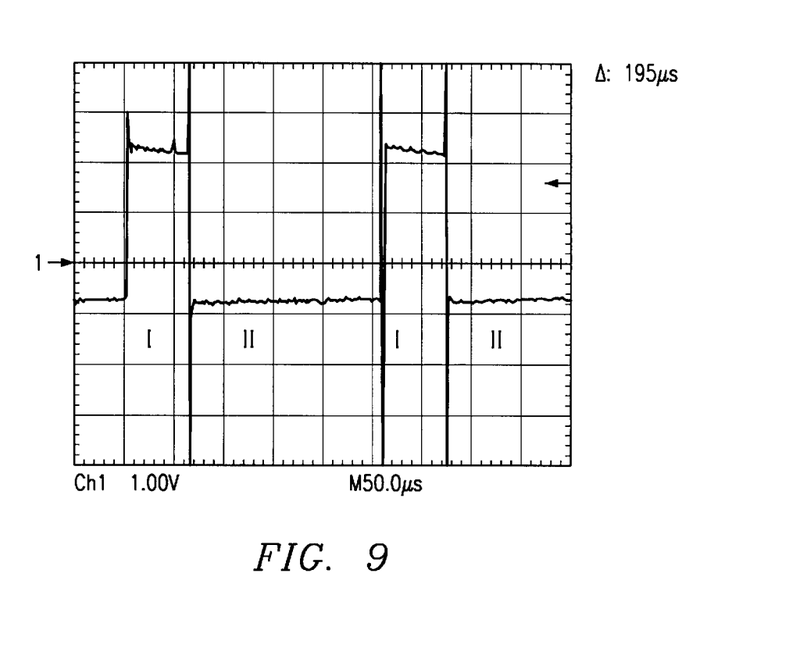
FIG. 9 shows an example of the waveform that the transducer coil of the present invention generates.

FIG. 9 shows an example of the waveform that the transducer coil of the present invention generates. Note that the high voltage is one-third the duration and three times the magnitude of the low voltage. FIG. 9 shows the PEMF stimulation signal output from PEMF winding 92 which includes a pulse portion I followed by pulse portion II. Pulse portion I has a duration of approximately 65 microseconds. Pulse portion II has a duration of approximately 195 microseconds. The voltage level for pulse portion I is approximately three times the voltage level for portion II. The areas of the portions I and II, therefore, are approximately equivalent. As explained below, the pulse periods (260 microseconds) and pulse frequency (3.84 kilohertz) of the output signal are in response to pulsed control signals.

Figure 10:
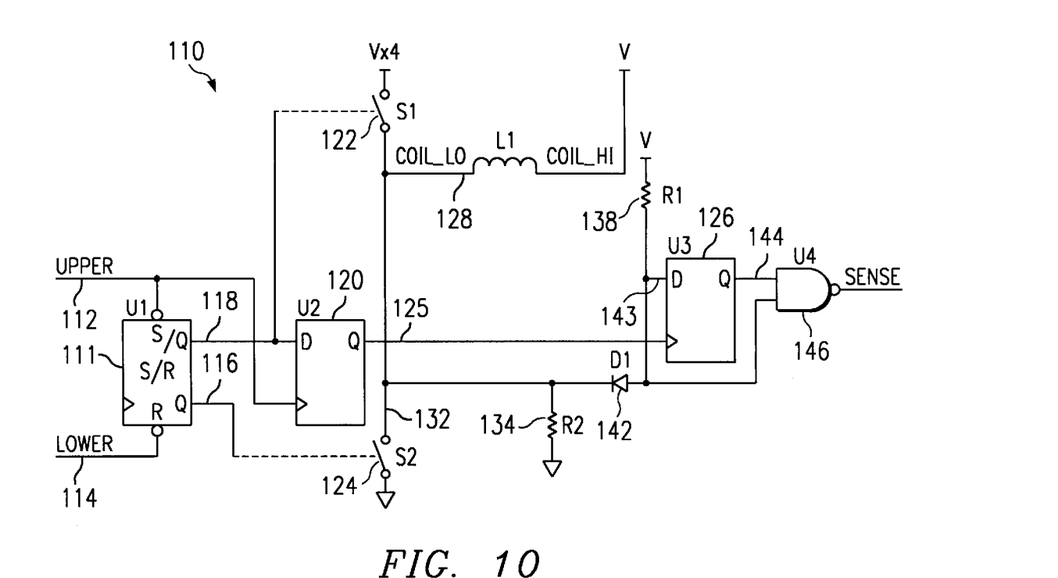
FIG. 10 shows a schematic diagram of the coil break detection circuit of the present invention.

FIG. 10 provides one embodiment of the system of FIG. 8 that uses digital circuitry of coil break detection circuit 82 that detects a field-fault condition in the PEMF stimulation therapy device of the present invention. The digital circuitry 110 includes U1 set/reset flip-flop 111 that receives upper input 112 and lower input 114 to output Q output 116 and /Q output 118. The /Q output 118 goes to U2 flip-flop 120 and controls the operation of S1 switch 122. The Q output 116 controls the operation of S2 switch 124. The Q output 125 from U2 flip-flop 120 goes to U3 flip-flop 126 as a clock signal. The S1 switch 122 controls whether the COIL-LO from L1 field winding 128 goes to $V_{X4}$ while S2 switch 124 shunts COIL-LO from L1 field winding 128 to ground. The COIL_HI line provides supply voltage V to L1 field winding 128.

Line 132 between S1 switch 122 and S2 switch 124 connects to R2 resistor 134 and D1 diode 142, which receives supply voltage, V, from R1 resistor 138. U3 flip-flop 126 receives as its D input 143 the output from R1 resister 138. The Q output 144 from U3 flip-flop 126 goes to U4 NAND gate 146 to generate a sense output.

In operation, digital circuitry 110 has drive circuit elements including U1 flip-flop 111, S1 switch 122, S2 switch 124, and L1 field winding 128. The voltage $V_{X4}$ is four times the voltage V, both being measured with respect to ground. The UPPER and LOWER signals consist of a burst of pulses, separated by an inter-burst period, as shown in FIG. 11. These two signals are essentially non-overlapping ensuring the stable operation of the U1 set-reset flip-flop, 111.

The Q and /Q outputs of U1 set/reset flip-flop 111 are of opposite state and are also essentially non-overlapping, ensuring S1 switch 122 and S2 switch 124 are never simultaneously conducting.

The coil break detection circuitry components of digital circuitry 110 include U2 flip-flop 120, U3 flip-flop 126, U4 NAND gate 146, D1 diode 142, R1 resistor 138, and R2 resistor 134. The COIL_LO signal, with L1 field winding 128 in place, is as shown in FIG. 11. During the burst, COIL_LO transitions between $V_{X4}$ and Ground.

During the inter-burst period, both S1 switch 122 and S2 switch 124 are open. Under normal operating conditions, L1 field winding 128 will pull the COIL_LO signal level to the supply voltage V. If a break should occur in the coil, the COIL LO signal will be pulled to ground by R2 resistor 134.

R1 resistor 138, R2 resistor 134 and D1 diode 142 translate the COIL_LO signal to levels appropriate for the inputs of U3 flip-flop 126 and U4 NAND gate 146. The ratio of R1 resistor 138 to R2 resistor 134 is selected to provide a logic level "0" at the inputs of U3 flip-flip 126 and U4 NAND gate 146 should a break occur in L1 field winding 128.

The output of U2 flip-flop 120 is a single pulse occurring at the beginning of a burst, beginning with the first pulse of UPPER and terminating on the second pulse of UPPER. The rising edge of the output of U2 flip-flop 120 occurs prior to the first rising edge of COIL_LO due to the relatively short time delay associated with U2 flip-flop 120 versus S1 switch 122 and S2 switch 124. The sampling pulse output of U2 is fed to U3 which samples the inter-burst voltage. If the inter-burst voltage is equal to V, the Q output 144 of U3 flip-flop 126 will be set to a logic level "1" until the next sampling pulse, thereby enabling output of the inverse of the COIL-LO signal to the processor as the SENSE signal.

If the inter-burst voltage is at a ground level, due to a break in L1, the output of U3 will be set to a logic level "0", disabling the output of the inverse of the COIL LO signal to the processor.

A short across the coil terminals will cause the COIL_LO signal to be tied to V. The output of U3 flip-flop 126 will be a logic level "1," therefore the output of U4 NAND gate 146 will be a logical level "0" rather than the burst signal that PEMF microcontroller 62 normally expects. This indicates the existence of a field fault condition to the PEMF microcontroller 62.

Connecting either the COIL_HI or COIL_LO terminal to ground, will essentially create a DC short of the power to the unit and a loss of power.

Figure 11:
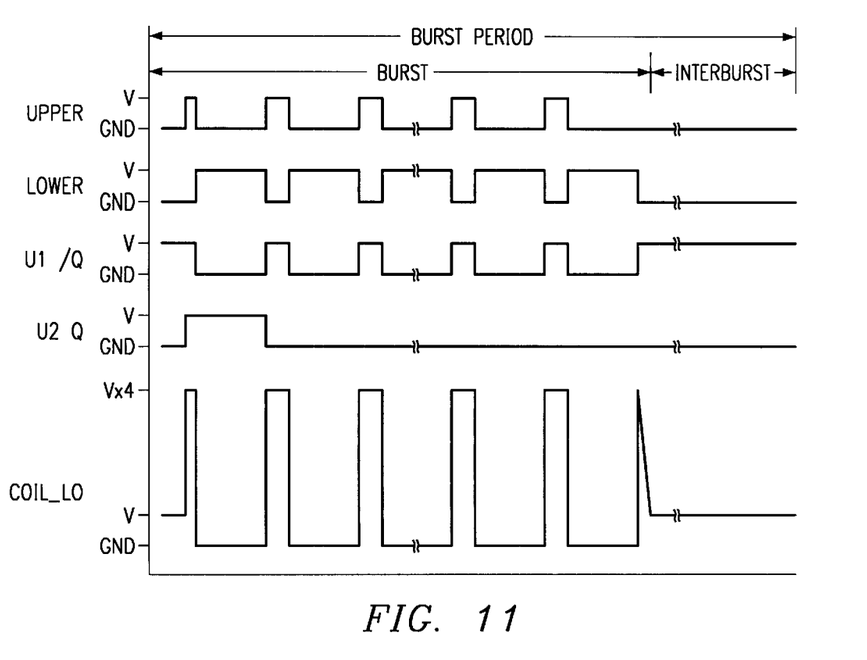
FIG. 11 shows a diagram of the input logic burst signal of the present invention.

FIG. 11 shows a diagram of the logic burst signal of the present invention, that in greater detail depicts the duration relationship between the upper and lower logic signals. In each logic burst signal, there are a number of pulses, the duration of each upper pulse being only one-third the duration of lower pulse. Other parameters may also be used.

Figure 12:
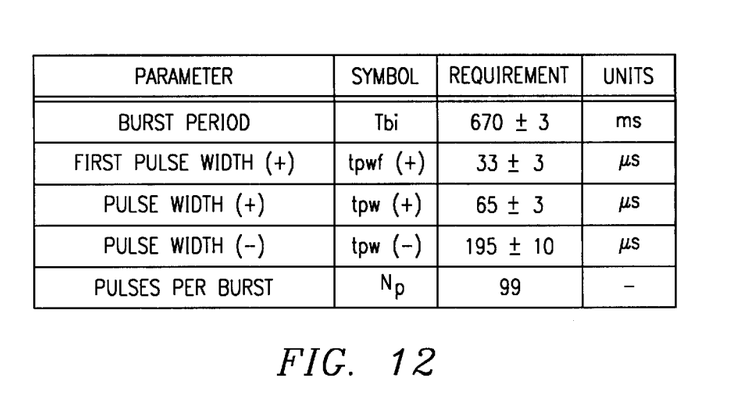
FIG. 12 provides a table of typical parameters, requirements, units, and symbols that correspond to the diagrams of FIGS. 9 and 11.

FIG. 12 provides a table of parameters, requirements, units, and symbols that correspond to the diagrams of FIG. 11. In the table of FIG. 12, the burst period is 670 milliseconds, during which a first pulse width is 33 microseconds. Thereafter the upper pulse width is 65 microseconds. The lower pulse width is 195 microseconds. The pulse period is 260 microseconds for a pulse frequency of 3.84 kilohertz. For the example of FIG. 12, which produces the input that FIG. 11 depicts, there are 99 pulses per burst. The present invention may also use other timing parameters to achieve the desired PEMF signals and associated energy recovery operation.

4. High Frequency Drive Signal Operation

As stated above, the use of only a single primary coil results in increased efficiency of transducer 20, as compared to designs using more than one coil. For the output PEMF signal described above, the energy recovery capacitance circuit 100 provides an energy recovery voltage of four times the source voltage provided by battery 84. As explained above, both the source voltage (V) and the energy recovery voltage ($V_{4X}$) are lower than the voltages required for previous designs. Thus, the requirements for the capacitance circuit 100 are also relaxed.

A feature of transducer 20 is that its efficiency increases as a function of the drive signal frequency. Thus, high frequency control signals may be used to further lower the energy requirements of transducer 20.

Referring again to FIG. 11, examples of high frequency pulse widths for the ON/OFF states of the control signals are 4 microseconds and 12 microseconds, for a pulse period of 16 microseconds. The ON/OFF ratio of the pulses are the same (3:1 and 1:3), as are the duration of the pulse burst and of the interval between bursts. Thus, the control signal has the same burst period and therefor the same net PEMF stimulation output. The 16 microsecond pulse period provides an output signal frequency of 62.5 kilohertz, as compared to the 3.84 kilohertz frequency of the 260 microsecond pulse period. In general, a pulse period in the order of 10 microseconds is considered "high frequency" for purposes of this invention. Referring again to FIG. 9, for the high frequency mode of operation, the output signal would have a pulse period and pulse frequency corresponding to that of the drive signals.

For the high frequency drive signals, the same energy recovery capacitance circuit 100 may be used. However, because the higher frequency signal is more efficient in terms of energy used by inductor 92, the capacitances of the capacitors 100a and 100b can be lower. For example, where frequency is higher by a factor of 15, the capacitance can be theoretically reduced by a factor of 15. In practice, other circuit considerations will make the actual capacitance reduction somewhat less.

5. Soft Tissue Growth Stimulation

Because of its energy efficiency, transducer 20 may be made smaller and lighter than existing PEMF stimulators. These characteristics increase the versatility of transducer 10. Various transducer housings can be configured for tissue growth stimulation as well as bone growth stimulation. Bone growth stimulation devices can be configured for fresh fractures as well as for delayed union and non-union fractures. Compact and lightweight devices can be incorporated into casts, bandages, or applied directly to anatomical areas that would be difficult to treat with a bulky and heavy device.

In addition to smaller battery size, smaller coil size, and smaller capacitances, the coil wiring is less constrained. As explained above, the increased efficiency of transducer 20 creates a desired electromagnetic field with a decreased amount of current. The lower current load through the transducer coil allows the coil wiring of previous embodiments to be replaced with circuitry applied to a flexible substrate. For example, the coil can be manufactured with techniques similar to those used for printed circuit boards.

Figure 13:
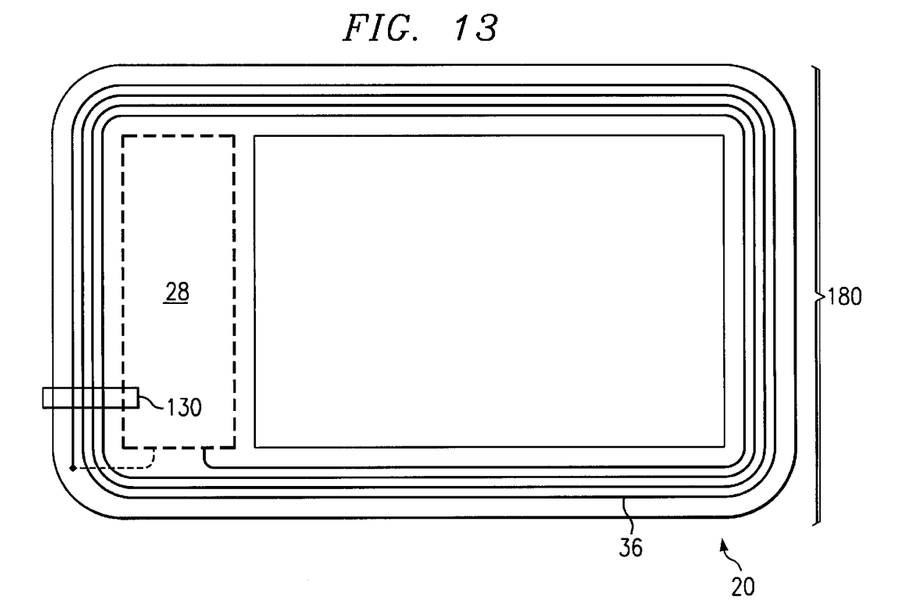
FIG. 13 illustrates a PEMF therapy system incorporating teachings of the present invention especially suitable for healing fresh bone fractures and soft tissue.

FIG. 13 is a schematic of a "flexible coil" PEMF therapy system according to one embodiment of the present invention. PEMF transducer 20 comprises transducer coil 36 and associated drive electronics 28, as in previous embodiments. In the embodiment shown, transducer coil 36 comprises wire printed directly onto a flexible substrate 180. For example, printed wire fabrication techniques, generally known in the art, could imprint the wire that forms transducer coil 36 onto a MYLAR substrate. Drive circuitry 28 could also be encapsulated onto flexible substrate 180, or contained in a plastic housing operable to snap onto flexible substrate 180.

For example, a flexible coil 36 could be placed under or integrated into a cast for a fractured bone. Similarly, a flexible coil 36 could be used with bandaging for a skin wound.

A transducer 20 having a flexible coil 36 and used with a cast or bandage would be further enhanced with a special "pull type" on/off tab 130. The user would simply pull the tab to activate processor 62 and begin operation of the drive circuit 90. The use of pull tab 130 would permit all control electronics 60 and drive circuitry 90 to be embedded into the cast or bandage.

6. Series-Connected Coils

Figure 14:
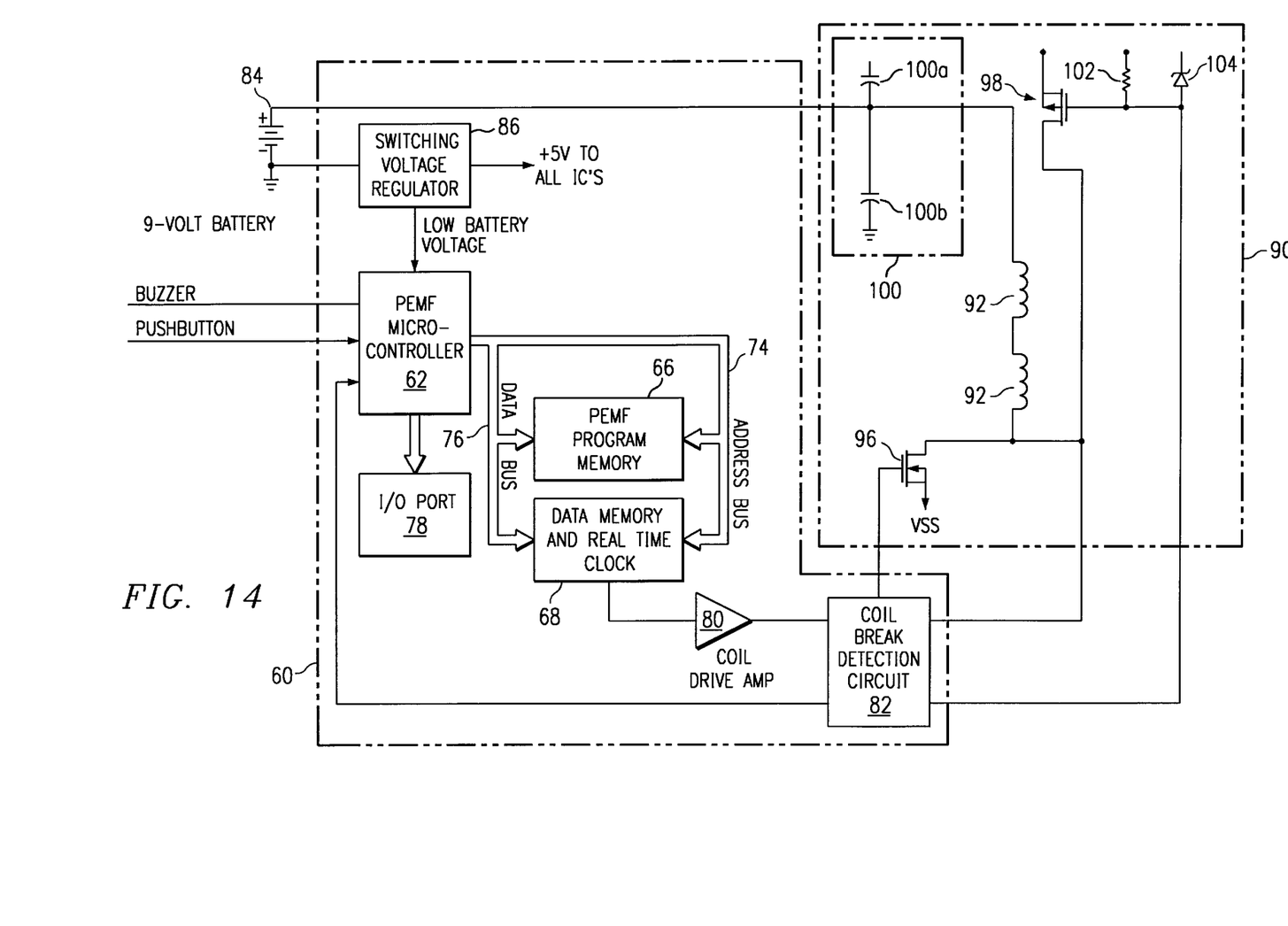
FIG. 14 is a schematic block diagram of the control electronics and the drive electronics for series-connected coils.

FIG. 14 illustrates an alternative embodiment of drive electronics 90, where transducer 20 is comprised of two inductor coils 92 in series. The coils 92 are energized and then de-energized in the same bi-phasic manner as described above for the single-coil embodiments. Current runs in one direction through both coils 92, and then reverses and runs in the other direction through both coils. Thus, the two coils 92 carry the same current at a given phase of the drive signals, and the need for "secondary" coils is eliminated by an energy recovery circuit 100. The same concepts could be applied to any number of series-connected coils.

Figure 15:
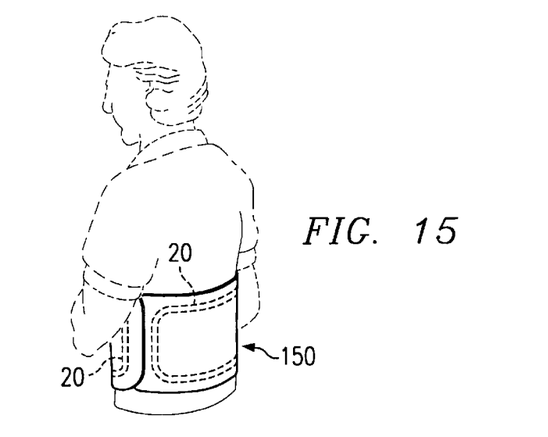
FIG. 15 illustrates a PEMF therapy system formed with series-connected coils.
Figure 16:
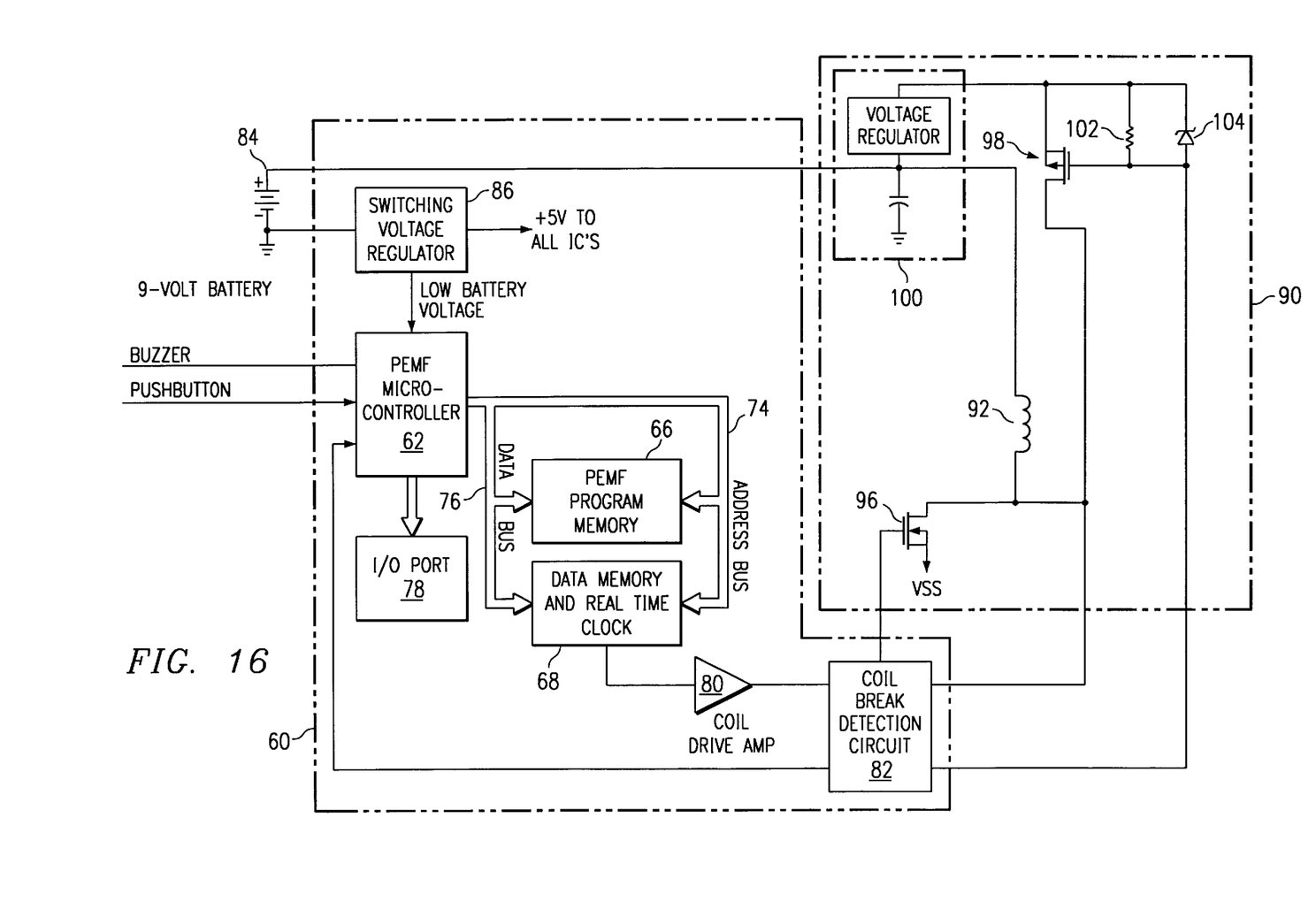
FIG. 16 illustrates an alternative embodiment of the capacitance circuit of FIGS. 8 and 14.

FIG. 15 illustrates an application of a transducer 150 having series-connected coils 92. Transducer 150 is used for treating spinal injuries. The transducer 150 is placed in a fabric or other soft material that may be wrapped around the patient's waist. One of the coils 92 is placed against the patient's back and one against the patient's abdomen. For example, one coil 92 could be centered about the lumbar region and the other about the navel.

Transducer 150 may be used in any of the above-described applications. For example, it may be encased in a semi-rigid housing. Or, it may be printed on a flexible substrate, which is the case for the example of FIG. 15.

7. Conclusion.

Although the invention has been described with respect to a specific, exemplary embodiment, various changes and modifications may be suggested to one skilled in the art. For example, the control and drive electronics may be different from those of the above-described embodiments. In such an alternative embodiment, for example, the control and drive electronics may be detached from the PEMF transducer 20 with an electrical cord existing there between. Therefore, it is intended that the invention encompass all changes and modifications that fall within the scope of the appended claims.

What is claimed is:

1. A PEMF transducer for a tissue stimulator device, comprising:

at least one transducer coil for generating a PEMF stimulation signal in response to bi-directional drive signals;

a drive circuit for providing said drive signals, namely a first drive signal to said coil in a first direction and a second drive signal to said coil in a second direction, said first drive signal being at a supply voltage and said second drive signal being at an energy recovery voltage, said drive circuit having energy recovery means for recovering flyback energy from said coil and for providing said energy recovery voltage; and a control circuit for switching between said first drive signal and said second drive signal;

wherein said drive circuit, said energy recovery circuit, and said control circuit are attached adjacent to said coil, such that the transducer is a single integrated unit.

2. The PEMF transducer of claim 1, wherein said energy recovery voltage is approximately four times said supply voltage.

3. The PEMF transducer of claim 1, wherein said control circuit provides an upper logic signal and a lower logic signal, each comprising a burst of pulses, said upper logic signal and lower logic signal having opposite states for controlling said first and said second drive signals.

4. The transducer of claim 1, wherein said energy recovery circuit is comprised of at least one capacitor.

5. The transducer of claim 1, wherein said energy recovery circuit is comprised of at least two series connected capacitors.

6. The transducer of claim 1, wherein said energy recovery circuit is comprised of at least one capacitor and a voltage regulator.

7. The transducer of claim 1, further comprising a flexible substrate and wherein said coil is embedded in said flexible substrate.

8. The transducer of claim 1, further comprising a flexible substrate and wherein said coil is applied to said flexible substrate.

9. The transducer of claim 1, further comprising a pull tab for activating said control circuit.

10. The transducer of claim 1, wherein said coil has a single set of primary coil windings.

11. The transducer of claim 1, wherein said coil has multiple sets of series-connected primary coil windings.

12. The transducer of claim 1, wherein said coil has multiple sets of parallel-connected primary coil windings.

13. A PEMF transducer for a tissue stimulator device, comprising:

two or more series-connected transducer coils for generating a PEMF stimulation signal in response to bi-directional drive signals;

a drive circuit for providing said drive signals, namely a first drive signal to said coil in a first direction and a second drive signal to said coil in a second direction, said first drive signal being at a supply voltage and said second drive signal being at an energy recovery voltage, said drive circuit having energy recovery means for recovering flyback energy from said coil and for providing said energy recovery voltage; and a control circuit for switching between said first drive signal and said second drive signal;

wherein said drive circuit, said energy recovery circuit, and said control circuit are attached adjacent to said coil, such that the transducer is a single integrated unit.

14. The PEMF transducer of claim 13, wherein said energy recovery voltage is approximately four times said supply voltage.

15. The PEMF transducer of claim 13, wherein said control circuit provides an upper logic signal and a lower logic signal, each comprising a burst of pulses, said upper logic signal and lower logic signal having opposite states.

16. The transducer of claim 13, wherein said energy recovery circuit is comprised of at least one capacitor.

17. The transducer of claim 13, wherein said energy recovery circuit is comprised of at least two series connected capacitors.

18. The transducer of claim 13, wherein said energy recovery circuit is comprised of at least one capacitor and a voltage regulator.

19. The transducer of claim 13, further comprising a flexible substrate and wherein said coils are embedded in said flexible substrate.

20. The transducer of claim 13, further comprising a flexible substrate and wherein said coils are applied to said flexible substrate.

21. The transducer of claim 13, further comprising an actuator for activating said control circuit.

22. A triangular loop device for applying electromagnetic field therapy to tissue; comprising:

at least one transducer coil having a generally triangular loop shape, said coil operable as a primary coil to carry bi-directional current a nd to generate an electromagnetic field in response to a pulsed electrical drive signal;

a coil shell having substantially the same triangular loop shape as said coil;

a electrical circuitry housing attached to said coil shell; and electrical circuitry contained within said housing for generating said pulsed electrical drive signal.

23. The device of claim 22, wherein said coil is made from a first material having a first flexible property and said shell is made from a second material having a second flexible property.

24. The device of claim 22, wherein said coil is made from a deformable material having properties such that said coil may take a desired shape in response to pressure and to hold said shape when said pressure is released and wherein said shell is sufficiently flexible to permit said desired shape.

25. The device of claim 22, wherein said shell is made from a material having properties such that said coil may take a desired shape in response to pressure and to hold said shape when said pressure is released and wherein said coil is sufficiently flexible to permit said desired shape.

26. The device of claim 22, wherein said housing is adjacent said coil and said shell such that the profile of said device is substantially the same as said shell.

27. The device of claim 22, wherein said electrical circuitry has an energy recovery circuit for recovering flyback energy from said coil and for providing an energy recovery voltage for said coil.

28. The device of claim 22, wherein said coil has a single set of primary coil windings.

29. The device of claim 22, wherein said coil has multiple sets of series-connected primary coil windings.

30. The device of claim 22, wherein said coil has multiple sets of parallel-connected primary coil windings.

31. A band type device for applying pulsed electromagnetic field (PEMF) therapy to tissue; comprising:

at least one transducer coil, said coil operable as a primary coil to carry bi-directional current and to generate an electromagnetic field in response to a pulsed electrical drive signal, said coil being made from a first flexible material having a first flexible property such that it may be set to a desired curvature in response to an applied pressure and to maintain said curvature when said pressure is released;

a coil shell that encloses said coil, said shell being made from a second flexible material having a second flexible property, such that said coil shell permits said desired curvature;

an electrical circuitry housing attached adjacent to said coil shell; and electrical circuitry contained within said housing for generating said pulsed electrical drive signal, said electrical circuitry having an energy recovery circuit for recovering flyback energy from said coil and for providing said bi-directional current;

wherein said coil has multiple sets of series-connected primary coil windings.

32. An oval loop device for applying electromagnetic field therapy to tissue, comprising:

at least one transducer coil having a generally oval loop shape, said coil operable as a primary coil to carry bi-directional current and to generate an electromagnetic field in response to a pulsed electrical drive signal;

a coil shell having substantially the same oval loop shape as said coil;

an electrical circuitry housing attached to said coil shell; and electrical circuitry contained within said housing for generating said pulsed electrical drive signal;

said electrical circuitry further comprising an energy recovery circuit for recovering flyback energy from said coil and for providing an energy recovery voltage for said coil.

33. The device of claim 32, wherein said coil is made from a first material having a first flexible property and said shell is made from a second material having a second flexible property.

34. The device of claim 32, wherein said coil is made from a deformable material having properties such that said coil may take a desired shape in response to pressure and to hold said shape when said pressure is released and wherein said shell is sufficiently flexible to permit said desired shape.

35. The device of claim 32, wherein said shell is made from a deformable material having properties such that said coil may take a desired shape in response to pressure and to hold said shape when said pressure is released and wherein said coil is sufficiently flexible to permit said desired shape.

36. The device of claim 32, wherein said housing is adjacent said coil and said shell such that the profile of said device is substantially the same as the profile of said shell.

37. The device of claim 32, wherein said electrical circuitry has an energy recovery circuit for recovering flyback energy from said coil and for providing and energy recovery voltage for said coil.

38. The device of claim 32, wherein said coil has a single set of primary coil windings.

39. The device of claim 32, wherein said coil has multiple sets of series-connected primary coil windings.

40. The device of claim 32, wherein said coil has multiple sets of parallel-connected primary coil windings.

41. A method of treating injured tissue, comprising the steps of:

applying a bandage in the area of said injured tissue;

placing at least one transducer coil adjacent said bandage, said coil operable to generate a PEMF stimulation signal in response to bi-directional drive signals, said coil having an associated drive circuit, energy recovery circuit, and control circuit; and activating said drive circuit by means of a pull tab extending from said bandage.

42. The method of claim 41, wherein said bandage has multiple layers and said coil is adjacent one or more layers such that said coil is embedded in said bandage.

43. The method of claim 41, wherein said tissue is hard tissue and said bandage is a rigid cast.

44. The method of claim 43, wherein said coil is embedded in said cast.

45. The method of claim 41, wherein said control circuit further has a processor and timing circuitry for energizing said coil according to a predetermined treatment schedule.

46. The transducer of claim 21, wherein the actuator is a pull tab.

* * * * *

UNITED STATES PATENT AND TRADEMARK OFFICE
CERTIFICATE OF CORRECTION

PATENT NO. : 6,261,221 B1
DATED : July 17, 2001
INVENTOR(S) : John C. Tepper, Peter Kuo and William Winstrom It is certified that error appears in the above-identified patent and that said Letters Patent is hereby corrected as shown below:

<u>Title page,</u>
Item [75], Inventors, please delete "William Winstrom" and insert
-- William L. Winstrom --.

Signed and Sealed this

Ninth Day of April, 2002

Attest:

JAMES E. ROGAN
*Attesting Officer*     *Director of the United States Patent and Trademark Office*